United States Patent [19]
Silvestrini

[11] Patent Number: 5,944,752
[45] Date of Patent: *Aug. 31, 1999

[54] ASTIGMATIC CORRECTING INTRASTROMAL CORNEAL INSERT

[75] Inventor: Thomas A. Silvestrini, Alamo, Calif.

[73] Assignee: Kera Vision, Inc., Fremont, Calif.

[ * ] Notice: This patent is subject to a terminal disclaimer.

[21] Appl. No.: 08/932,731

[22] Filed: Sep. 17, 1997

Related U.S. Application Data

[63] Continuation of application No. 08/386,920, Feb. 9, 1995, abandoned, which is a continuation of application No. 08/163,650, Dec. 6, 1993, Pat. No. 5,405,384, which is a continuation-in-part of application No. 07/939,492, Sep. 3, 1992, abandoned.

[51] Int. Cl.$^6$ ........................................................ A61F 2/14
[52] U.S. Cl. ........................................................ 623/5; 623/4
[58] Field of Search ............................. 623/4, 5; 606/107, 606/166, 167

[56] References Cited

U.S. PATENT DOCUMENTS

| | | | |
|---|---|---|---|
| 4,671,276 | 6/1987 | Reynolds | 606/166 |
| 4,781,187 | 11/1988 | Herrick | 623/5 X |
| 5,300,118 | 4/1994 | Silvestrini et al. . | |
| 5,318,047 | 6/1994 | Davenport | 128/898 |
| 5,372,580 | 12/1994 | Simon et al. | 604/107 X |
| 5,405,384 | 4/1995 | Silvestrini . | |
| 5,466,260 | 11/1995 | Silvestrini et al. . | |
| 5,653,752 | 8/1997 | Silvestrini et al. . | |
| 5,693,092 | 12/1997 | Silvestrini et al. . | |
| 5,824,086 | 10/1998 | Silvestrini . | |

FOREIGN PATENT DOCUMENTS

| | | |
|---|---|---|
| 388746 | 7/1993 | Russian Federation . |
| WO 95/17144 | 6/1995 | WIPO . |

OTHER PUBLICATIONS

English translation of Brazilian Patent Application No. BR 8705060 (Mar. 21, 1989).

D'Hermies et al., "Biocompatibility of a refractive intracorneal PMMA ring" *Fortschr. Ophthalmol.* (1991) 88:790–793.

*Primary Examiner*—Mickey Yu
*Assistant Examiner*—Dinh X. Nguyen
*Attorney, Agent, or Firm*—Morrison & Foerster Inc.

[57] ABSTRACT

This implant is an intrastromal corneal insert ("ICR") which is not uniform in dimension. It has, typically, two or more raised areas (or areas of additional bulk) spaced apart from each other on the insert. This insert design, when introduced into the stroma and properly adjusted there, permits at least partial correction of astigmatism in the eye.

40 Claims, 4 Drawing Sheets

ASTIGMATIC CORRECTING INTRASTROMAL CORNEAL INSERT

This application is a continuation of application Ser. No. 08/386,920, filed Feb. 9, 1995, now abandoned; which is a continuation of Ser. No. 08/163,650, filed Dec. 6, 1993, now U.S. Pat. No. 5,405,384; which is a continuation-in-part of Ser. No. 07/939,492, filed Sep. 3, 1992, now abandoned.

FIELD OF THE INVENTION

This invention is an intrastromal corneal insert ("ICR") or sector which is not dimensionally uniform about the insert. It has at least one area, or, more typically, two or more raised areas (or areas of additional bulk) spaced apart from each other on the insert. This insert design, when introduced into the stroma and properly adjusted for position there, permits at least partial correction of astigmatism in the eye.

BACKGROUND OF THE INVENTION

Anomalies in the overall shape of the eye can cause visual disorders. Hyperopia ("farsightedness") occurs when the front-to-back distance in the eyeball is too small. In such a case, parallel rays originating greater than 20 feet from the eye focus behind the retina. In contrast, when the front-to-back distance of eyeball is too large, myopia ("nearsightedness") occurs and the focus of parallel rays entering the eye occurs in front of the retina. Astigmatism is a condition which occurs when the parallel rays of light do not focus to a single point within the eye, but rather focus to a region due to the fact that the cornea is aspherical and refracts light in a different meridian at different distances. Some degree of astigmatism in an eye is normal, but where the astigmatism is too pronounced, it must often be corrected.

Hyperopia, myopia, and astigmatism are usually corrected by glasses or contact lenses. Surgical methods for the correction of such disorders are known. These methods include radial keratotomy (see, e.g., U.S. Pat. Nos. 4,815, 463 and 4,688,570) and laser corneal ablation (see, e.g., U.S. Pat. No. 4,941,093).

Another method for correcting those disorders is through the implantation of polymeric inserts in the eye's corneal stroma to change the curvature of the cornea. Previous work involving the implantation of polymethylmethacrylate (PMMA) inserts, allograft corneal tissue and hydrogels is well documented. One of the insert devices involves a split insert design which is inserted into a channel previously dissected in the stromal layer of the cornea. The device uses a minimally invasive incision through which the channel for the implant is created and, finally, through which the implant is inserted.

U.S. Pat. No. 4,452,235, to Reynolds, describes a method and apparatus for corneal curvature adjustment. The method involves inserting one end of a split end adjusting insert into the cornea of the eye and moving the insert in a circular path until its ends meet. The ends are thereafter adjusted relative to each other until the shape of the eye has assumed a desired curvature whereupon the ends are fixedly attached to maintain the desired curvature of the cornea.

Additionally, U.S. patent application Ser. No. 07/820,422, by Davenport et al., entitled "Method for Corneal Curvature Variation" suggests the use of ICRs for the correction of astigmatism. That disclosure does not suggest the use of ICRs having the inventive shape to alleviate astigmatism in the eye.

None of the prior art disclosures suggest the use of an ICR having a non-uniform shape about their periphery.

SUMMARY OF THE INVENTION

This invention is to a device, an astigmatic correcting intracorneal insert ("ACICR"), which is inserted into the interlamellar region of the eye's stroma. For the purpose of alleviating astigmatism, the device is an improvement over previously existing ICRs. Unlike other ICRs which have a constant cross-section when viewed through various cross-sections of the insert, the inventive ACICR typically has at least one region in which the cross-section is thicker or the bulk of that region is more pronounced. Often the inserts will have two or more regions at which the bulk is increased. Within the scope of this invention are partial inserts or sectors which encircle only a portion of the cornea. The partial inserts also may have variable cross-sections, but also may be of a constant thickness. By proper alignment of the larger regions of the ACICR or the partial sectors with the eye's anomalies, the astigmatism may be alleviated.

The devices for forming the intrastromal pathway into which these ICRs may be placed is well known.

DESCRIPTION OF THE INVENTION

Prior to explaining the details of the inventive devices, a short explanation of the physiology of the eye is needed to appreciate the functional relationship of the device to the eye.

Figure 1:
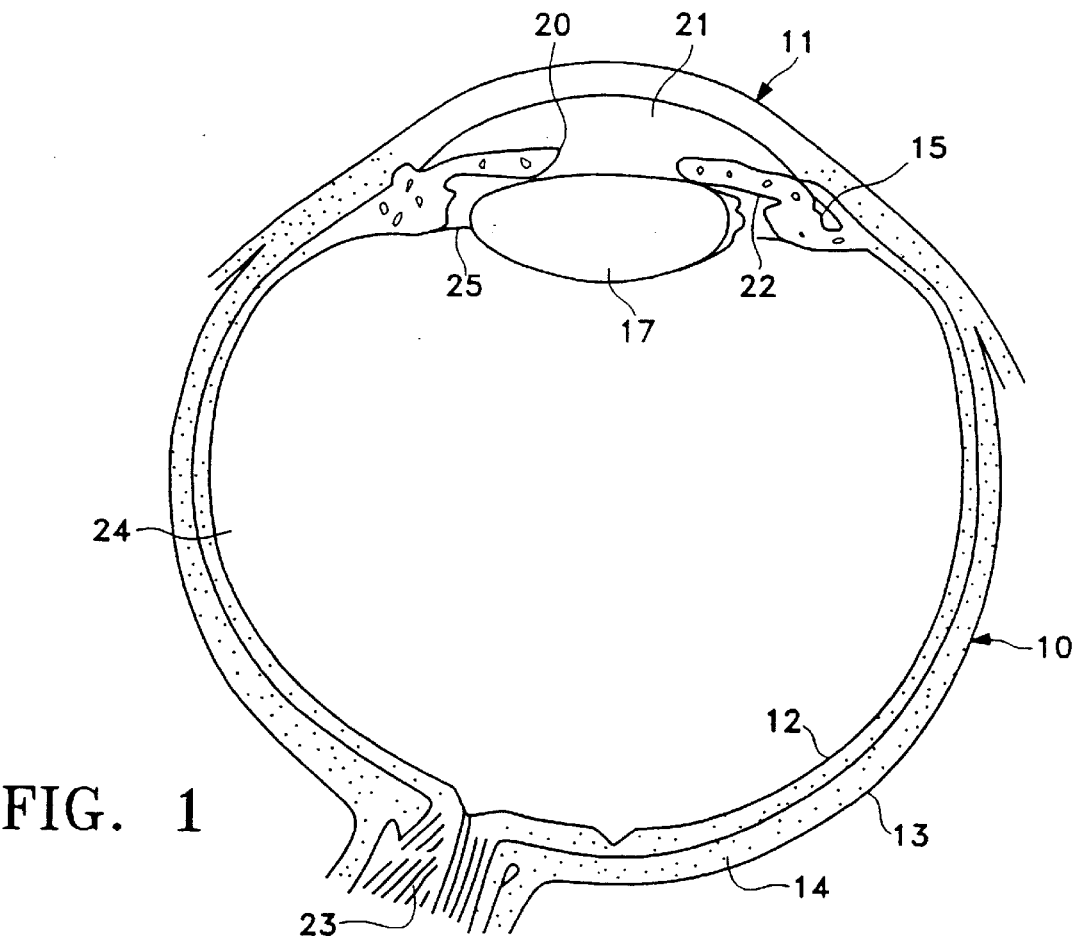
FIG. 1 is a schematic representation of a horizontal section of the eye.

FIG. 1 shows a horizontal section of the eye with the globe (10) of the eye resembling a sphere with an anterior bulged spherical portion representing the cornea (11).

The globe (10) of the eye consists of three concentric coverings enclosing the various transparent media through which the light must pass before reaching the light-sensitive retina (12). The outermost covering is a fibrous protective portion the posterior five-sixths of which is white and opaque and called the sclera (13), and sometimes referred to as the white of the eye where visible to the front. The anterior one-sixth of this outer layer is the transparent cornea (11).

A middle covering is mainly vascular and nutritive in function and is comprised of the choroid, ciliary body (15) and iris (20). The choroid (14) generally functions to maintain the retina (12). The ciliary body (15) is involved in suspending the lens (17) and accommodation of the lens. The iris (16) is the must anterior portion of the middle covering of the eye and is arranged in a frontal plane. It is a thin circular disc similar in function to the diaphragm of a camera, and is perforated near its center by a circular aperture called the pupil (20). The size of the pupil varies to regulate the amount of light which reaches the retina (12). It contracts also to accommodation, which serves to sharpen the focus by diminishing spherical aberration. The iris divides the space between the cornea (11) and the lens (17) into an anterior chamber (21) and posterior chamber. The innermost portion of covering is the retina (12), which is made up of nerve elements which form the true receptive portion for visual impressions.

The retina (12) is a part of the brain arising as an outgrowth from the fore-brain, with the optic nerve (23) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (24) is a transparent gelatinous mass which fills the posterior four-fifths of the globe (10). At its sides it supports the ciliary body (15) and the retina (12). A frontal saucer-shaped depression houses the lens.

The lens (17) of the eye is a transparent bi-convex body of crystalline appearance placed between the iris (16) and vitreous body (24). Its axial diameter varies markedly with accommodation. A ciliary zonule (25), consisting of transparent fibers passing between the ciliary body (15) and lens (17) serves to hold the lens (17) in position and enables the ciliary muscle to act on it.

Referring again to the cornea (11), this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place at the cornea.

Figure 2:
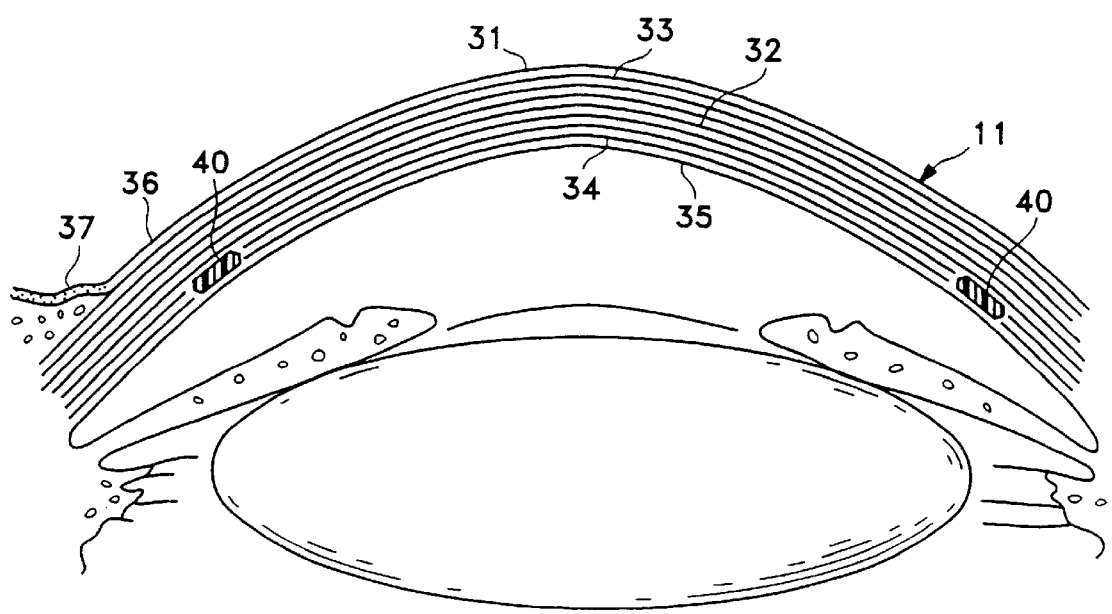
FIG. 2 is a schematic representation of the anterior portion of the eye showing the various layers of the cornea.

Referring to FIG. 2, a more detailed drawing of the anterior portion of the globe shows the various layers of the cornea (11) made up of an epithelium (31). Epithelial cells on the surface thereof function to maintain transparency of the cornea (11). These epithelial cells are rich in glycogen, enzymes, and acetylcholine and their activity regulates the corneal corpuscles and controls the transport of water and electrolytes through the lamellae of the stroma (32) of the cornea (11).

An anterior limiting lamina (33), referred to as Bowman's membrane or layer, is positioned between the epithelium (31) and the stroma (32) of the cornea. The stroma (32) is comprised of lamella having bands of fibrils parallel to each other and crossing the whole of the cornea. While most of the fibrous bands are parallel to the surface, some are oblique, especially anteriorly. A posterior limiting lamina (34) is referred to as Descemet's membrane. It is a strong membrane sharply defined from the stroma (32) and resistant to pathological processes of the cornea.

The endothelium (35) is the most posterior layer of the cornea and consists of a single layer of cells. The limbus (37) is the transition zone between the conjunctiva and sclera on the one hand and the cornea (11) on the other.

As has been explained above, most of the eye's refraction takes place at the outer portion of the cornea (12). The overall concept behind this invention is that by addition of selected amounts of bulk at the steeper portions of the anterior cornea or by inclusion of a non-uniform insert in radial tension, the anterior corneal surface will be forced into a generally spherical surface thereby correcting the undesired astigmatism.

Figure 3:
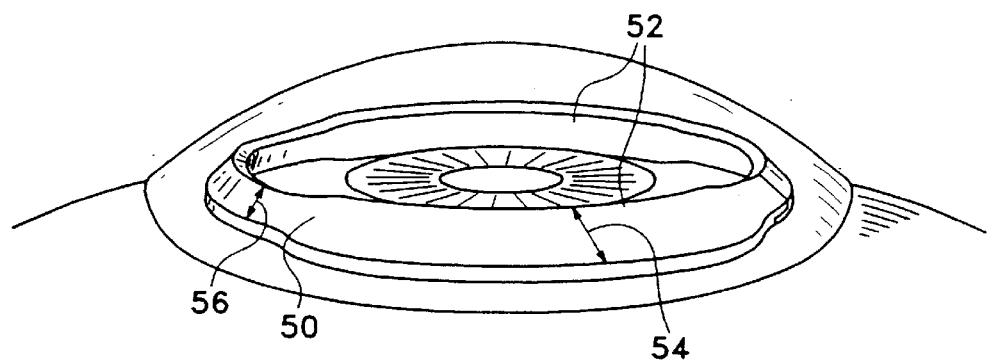
FIG. 3 depicts the inventive ACICR as it resides within the cornea.

FIG. 3 shows the placement of the non-regular ACICR within the cornea as discussed above. In this instance, the insert (50) has two regions (52) of added bulk or dimension. The larger regions in this instance have a larger relational width (54) than the local width of the narrower region (56). See also the side view of the comparative widths in FIG. 3. The relationship between the local widths (54) and (56), the thickness (58) at various positions of the ACICR, and their respective corrections, are known and may be determined from our U.S. patent appl. Ser. No. 07/820,472, filed Dec. 10, 1991.

Figure 5:
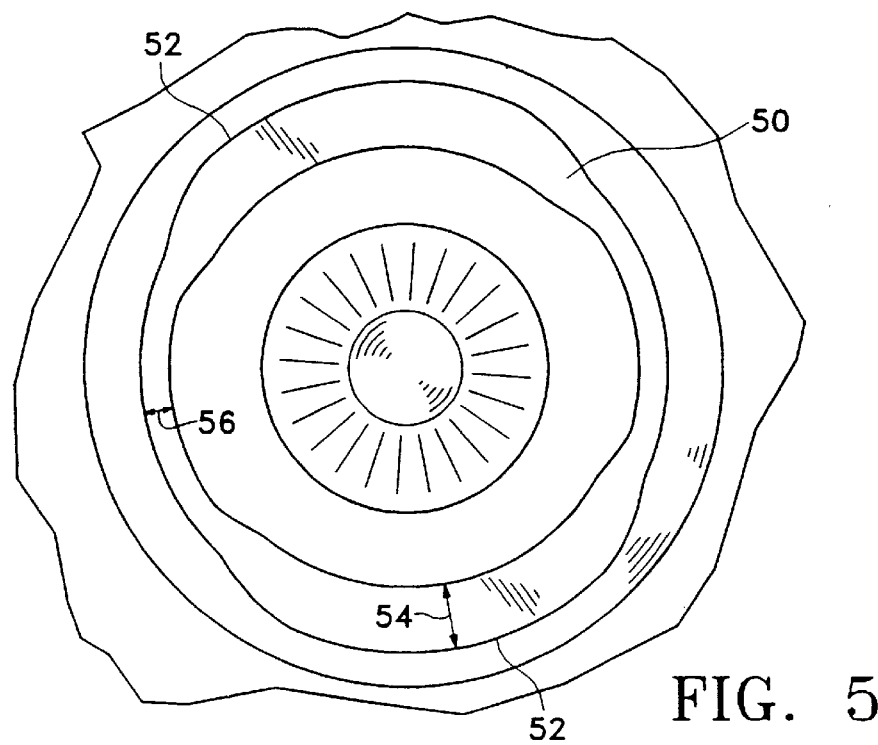
FIG. 5 is a frontal view showing the placement of the ACICR within the eye.

FIG. 5 is a frontal view of the eye having an ACICR installed. The insert (50) has two regions of added dimension (52). Those regions of added dimension would be placed in the regions of the cornea having the steepest slope in an effort to correct the cornea to an approximate spherical, or at least regular, shape about its anterior surface.

The regions of added dimension are critically tailored to correct the astigmatism found in a particular eye. In general, the regions (52) subtend an arc of at least about 2° measured from the center of the insert. More typically, the regions of larger dimension will subtend 10° to about 180° of an arc on the insert. The larger values are to remedy such conditions as keratoconus in which (typically) a significant angular portion the cornea is thinned or, at least, significantly lower (flatter) in profile than other portions of the cornea. Such regions typically subtend 15° to 45° of the insert arc in correction of typical astigmatic conditions. Consequently, for most conditions, the arc should be at least about 2°, preferably about 10° to 90°, more preferably about 20° to 45°, all however tailored to correction of the noted astigmatism in a particular eye. Special corrections up to 340°, although typically of up to 180°, of subtended arc are acceptable when special circumstances of astigmatism are encountered.

When multiple sections of added dimension are used, each section may be of the subtended arc sizes listed above for the single arcs. Clearly though, the sum of all of the subtended arcs for the must be less than 350° or so.

Figure 4:
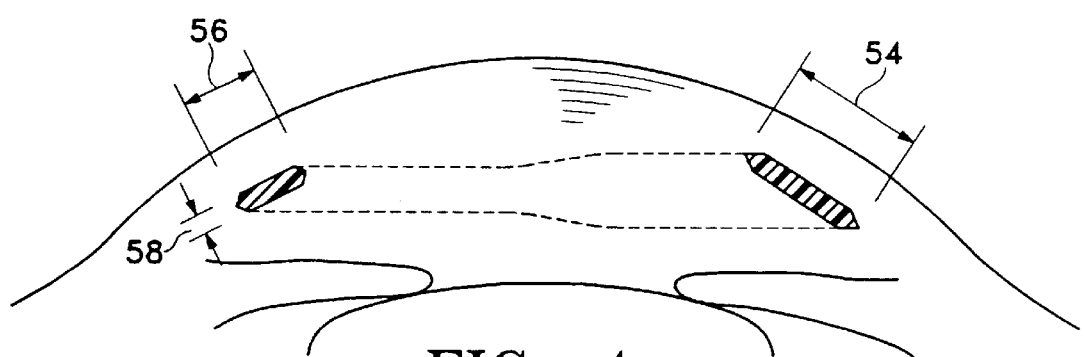
FIG. 4 is a side cross-section of the ACICR within the cornea.
Figure 6:
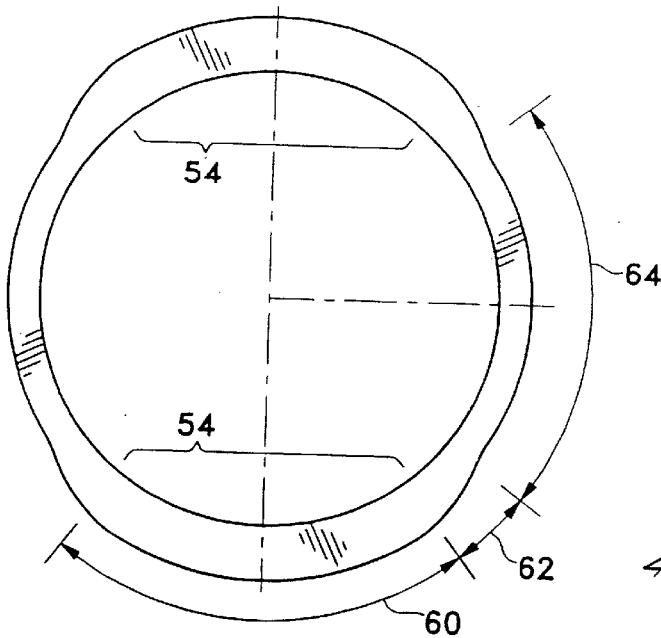
FIG. 6 is a frontal view of the ACICR having symmetrical areas of added bulk or cross-section.

FIG. 6 shows a frontal view of an ACICR in which the regions of added dimension are generally symmetrical. The regions of added dimension (54) are shown each to extend over a region of about 90° of the ACICR. FIG. 6 also shows a transition zone (62) between the area of added bulk 60 and the comparatively thinner region at (64). The transition zone allows the ACICR to be inserted into an intrastromal channel with greater ease. We believe this permits installation of the ACICR with less trauma. The arc (64) of lesser dimension is shown in FIG. 6. As with the local diameters (54) and (56) of the ACICR as shown in FIGS. 3 and 4, the percentage of arcs (60) and (64) and their respective relationship to each other are a function of the level of astigmatism to be corrected. The percentage of arcs of the areas of added dimension (60) and (64) are of the same relative sizes as discussed above in relation to FIG. 5.

Figure 7:
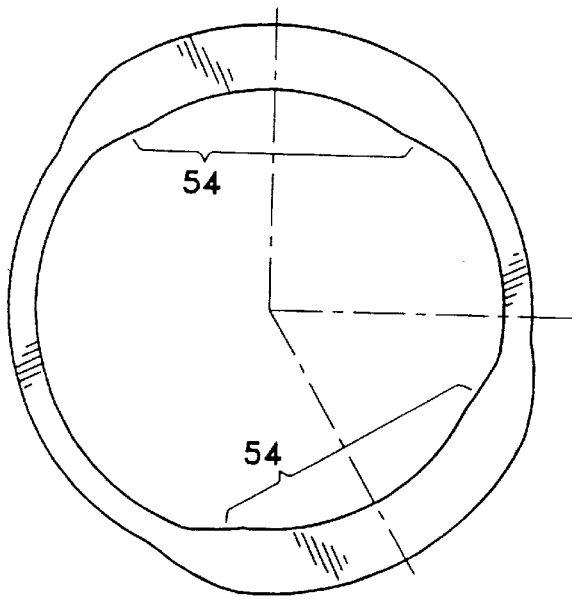
FIG. 7 is a frontal view of an ACICR having non-symmetric areas of added bulk or cross-section.

FIG. 7 shows an ACICR with regions of enhanced dimension which are not placed symmetrically about the insert.

Again, such a insert would be employed in an eye which did not have symmetrical astigmatism about a single axis. Such an ACICR would be employed with the intent to bring the corneal shape back into general spherical form.

Although we emphasize the use of inserts which encircle most of the cornea, such encirclement is not critical to the insertion. For instance, the ACICR may be a sector of a insert having an area or areas of varying thickness (or width) or, for some astigmatic maladies, a partial insert of a constant thickness or width properly placed may be an appropriate resolution of the malady. Each of the variations disclosed herein may be used in a variation covering as small an arc as 10°–15° of the corneal circumference.

Figure 8:
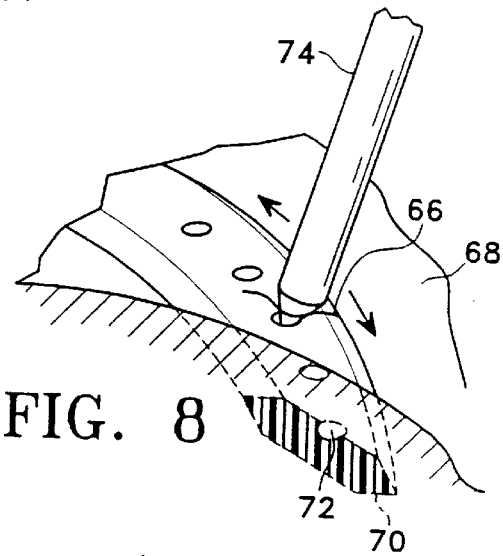
FIG. 8 depicts a feature of the invention which allows the ACICR to be manipulated into proper position for astigmatism correction.

The insert would be installed in the inner lamellar regions of the corneal stroma by any of the methods we have shown in the past to be suitable for such installation. Particularly desired is the process and its allied apparatus shown in U.S. Ser. No. 07/867,745, CORNEAL VACUUM CENTERING GUIDE AND DISSECTOR, filed Apr. 4, 1992. In general, the insert is installed in the following manner: a small radial incision is made at the radius in which the insert is ultimately to be installed about the cornea. A dissector in the form of a split insert and having a point suitable for producing an interlamellar channel or tunnel in the corneal stroma is introduced through the small incision and rotated in such a fashion that a generally circular channel is often (but not necessarily) formed completely about the cornea. The dissector is then rotated in the opposite direction to withdraw it from the tunnel thus formed. An ACICR is then introduced into the circular channel and joined at its ends. ICRs of constant cross-section typically need no further adjustment other than, perhaps, to move the point of junction away from the region of corneal incision so to help assure that the junction is held together by the interlamellar tension of the cornea. However, with an ACICR, the relationship of the insert and the astigmatic aberration must be aligned so to allow the ACICR to perform its desired correction. In FIG. 8, one such method for adjusting the position of the ACICR in the eye is shown. The radial incision (66) in cornea (68) which is used to introduce the ICR into the eye is shown. The ACICR (70) has a number of depressions (72) spaced about its upper surface. The position of the ACICR (70) is changed by engaging a generally pointed tool (74) into the depressions and slipping the insert (70) around in one direction or another until the regions of added dimension are in appropriate position for correcting the astigmatic aberrations of the cornea. Other variations on this will be apparent to those studying the need to adjust the position of these inserts.

Figure 9A:
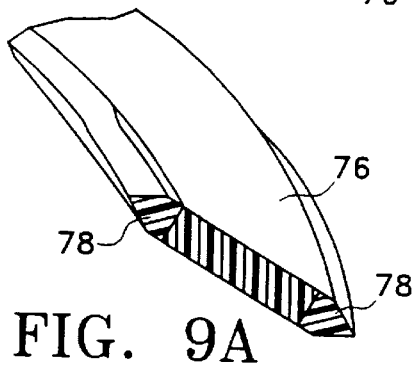
FIG. 9A shows a variation of the inventive ACICR using a composite insert in which a portion of the insert uses a swellable polymer, shown prior to being hydrated.
Figure 9B:
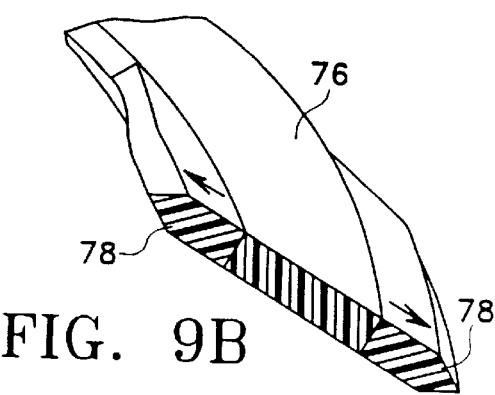
FIG. 9B illustrates the insert of FIG. 9A after being hydrated.

The materials used in these inserts are typically stiff physiologically acceptable polymers such as polymethylmethacrylate (PMMA), TEFLON, polycarbonate, polyolefins such as polyethylene, polypropylene, polybutylene, and their mixtures and interpolymers, or a silicone polymer or interpolymer such as are known in the art to be appropriately used in hard contact lenses. PMMA has a long history in ophthalmological usage and consequently is quite desirable for use in these ACICRs. However, another desirable variation is shown in FIGS. 9A and 9B. In this variation, the added dimension comprises a polymer which is swellable or expands upon continued contact with water. For instance, FIG. 9A shows a cross-section of an ACICR having a central portion (76) of a polymer such as PMMA and two regions (78) bonded to the inner and outer periphery of central portion (76). Outer portions (78) may be made of a crosslinked polymeric gel such as polyhydroxyethylmethylacrylate (Poly-HEMA) or polyvinylpyrrolidone (PVP). The extent of crosslinking in these polymers determines the extent to which the polymers will swell upon being exposed to water. In general, the higher the extent of crosslinking, the lower the volume increase upon contact with water. Some materials used in soft contact lenses will contain up to 99% by volume water. In any event, FIG. 9A shows the bonded outer portions (78) in their dehydrated condition (if the polymer is not highly crosslinked) and FIG. 9B shows those same outlying portions after insertion into the cornea and after they have been allowed to hydrate and swell. This variation of the inventive ACICRs allows the device to be inserted at a much smaller size but allows the insert to swell to correct much larger aberrations.

Figure 10:
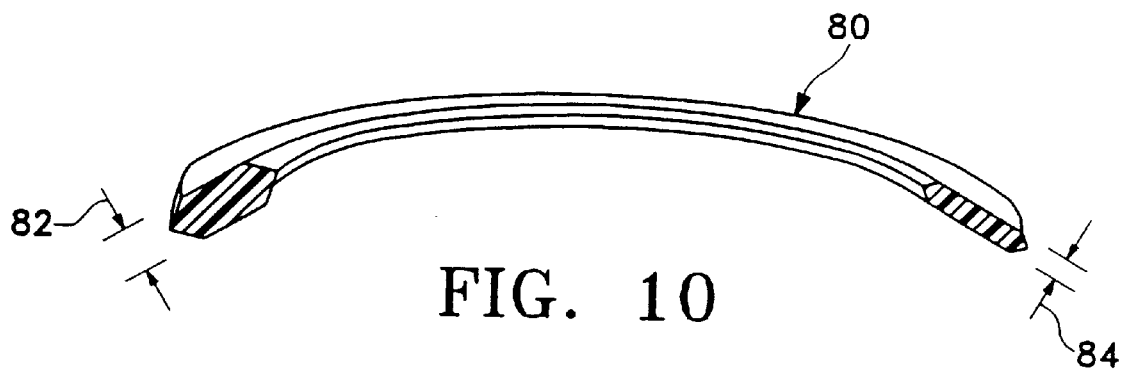
FIG. 10 shows an ACICR in which the thickness of the insert is varied.

The ACICR (80) shown in FIG. 10 is one in which the thickness of at least one portion of the regions is thicker (82) than another thinner portion (84) of the insert. As with the other ACICRs depicted in FIGS. 3–7, the number of thicker portions of the insert may be one or more depending upon the spherical aberration to be corrected. The typical ACICR likely will have two thicker regions about 180° apart on the insert. The insert may be between about 45° and more than about 140°. The portions of the arc which are thicker are also to be determined depending upon the astigmatism of the eye to be repaired.

Figure 11:
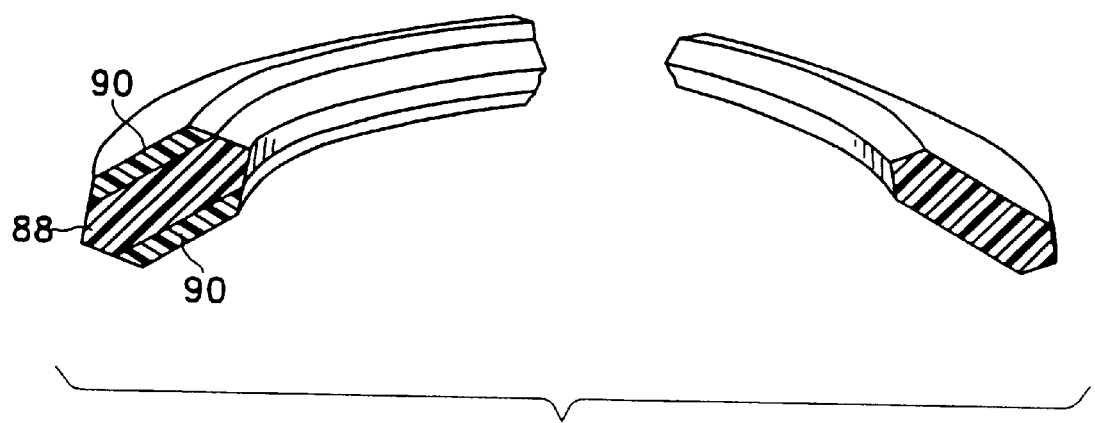
FIG. 11 shows an ACICR in which the insert is a composite of a stiff polymer and a swellable polymer.

FIG. 11 shows another variation of the ACICRs in which the insert is a composite assembly. The central portion (88) is of the one or more of the stiff polymers discussed above. The peripheral portions (90) comprise a swellable polymer which swells upon contact with moisture. As with the composite ACICRs above, they may be introduced into the eye prior to hydration, adjusted into proper position, and allowed to hydrate and swell into final shape.

The terms and expressions which have been used in the description above are used as terms of description and not of limitation. There is no intention of excluding equivalents of the features shown or described. It is recognized that one having ordinary skill in this art would perceive equivalents to the inventions claimed below which equivalents would be within spirit of the invention as expressed above.

I claim as my invention:

1. An intracorneal insert comprising first and second end portions and an arc-shaped body extending therebetween, said body having at least one enlarged portion with a transverse dimension greater than that of at least one portion of said body adjacent thereto and contiguous therewith, said insert configured to encircle only a portion of the cornea.

2. The insert of claim 1 wherein said body comprises at least two enlarged portions having transverse dimensions greater than those of said portions of said body adjacent thereto and contiguous therewith.

3. The insert of claim 1 wherein said transverse dimension is measured radially with respect to said body.

4. The insert of claim 1 further comprising means for adjusting the position of the insert when placed in the eye.

5. The insert of claim 1 further comprising depressions on a surface of said body.

6. The insert of claim 1 further comprising at least one transition zone adjacent to said enlarged portion, said at least one transition zone decreasing in dimension in a direction away from said enlarged portion.

7. The insert of claim 1 wherein said enlarged portion subtends more than about 2° of the arc of said body.

8. The insert of claim 7 wherein said enlarged portion subtends between about 10° and about 90° of the arc of said body.

9. The insert of claim 8 wherein said enlarged portion subtends between about 20° and about 45° of the arc of said body.

10. The insert of claim 1 wherein said body comprises one or more physiologically acceptable polymers.

11. The insert of claim 1 wherein said body comprises polymethylmethacrylate.

12. The insert of claim 1 wherein said body comprises a swellable polymer.

13. The insert of claim 12 wherein said enlarged portion is partially comprised of said swellable polymer.

14. An intrastromal corneal insert, said insert being arc-shaped and configured for encircling only a portion of the cornea, said insert having at least two enlarged portions with transverse dimensions greater than the transverse dimensions of the portions of the insert adjacent to and contiguous with said enlarged portions, said enlarged portions subtending more than about 2° of the arc of said insert.

15. The insert of claim 14 further comprising at least one transition zone adjacent to each said enlarged portion, each said transition zone decreasing in dimension in a direction away from said enlarged portion adjacent thereto.

16. The insert of claim 14 wherein the sum of said subtended enlarged portions is less than about 350° of the arc of said insert.

17. An intrastromal corneal insert configured for treating astigmatism, said insert being arc-shaped and configured for encircling only a portion of the cornea, said insert having at least one enlarged portion subtending an arc of no more than about 350 degrees, said enlarged portion having a transverse dimension greater than that of at least one portion of said insert adjacent thereto and contiguous therewith.

18. The insert of claim 17 wherein said at least one enlarged portion subtends an arc of between about 10° to about 180°.

19. The insert of claim 17 wherein said at least one enlarged portion subtends an arc of between about 10° to about 90°.

20. The insert of claim 17 comprising at least two enlarged portions having transverse dimensions greater than those of said portions of said insert adjacent thereto and contiguous therewith.

21. The insert of claim 5, wherein said depressions are adapted to receive a tool for adjustment of the placement of said insert.

22. The insert of claim 14, wherein said at least two enlarged portions include two of said enlarged portions spaced about 180° apart on said body.

23. The insert of claim 14, wherein said at least two enlarged portions are placed substantially symmetrically about said insert.

24. The insert of claim 14, wherein said at least two enlarged portions are placed substantially asymmetrically about said insert.

25. An intracorneal insert comprising an arc-shaped body having at least one enlarged portion with a dimension greater than that of at least one portion of said body adjacent thereto and contiguous therewith.

26. The intracorneal insert of claim 25, wherein said at least one enlarged portion subtends more than about 2° of the arc of said body.

27. The intracorneal insert of claim 25, wherein said body covers an arc of between about 45° and 140°.

28. The intracorneal insert of claim 25, wherein each of said at least one enlarged portion subtends about 10° to about 90° of the arc of said body.

29. The intracorneal insert of claim 28, wherein each of said at least one enlarged portion subtends about 20° to about 45° of the arc of said body.

30. The intracorneal insert of claim 25, wherein said at least one enlarged portion subtends up to 340° of the arc of said body.

31. The intracorneal insert of claim 28, wherein each of said at least one enlarged portion subtends up to 180° of the arc of said body and a sum of all of the enlarged portions subtend less than about 350° of the arc of said body.

32. An intracorneal insert having a periphery defining a substantially ring-shaped contour, said insert having at least one region of added dimension, said region of added dimension generally following said substantially ring-shaped contour and having at least one dimension greater than that of at least one region of said insert adjacent thereto and contiguous therewith.

33. The intracorneal insert of claim 32, wherein said insert is configured to encircle only a portion of the cornea.

34. The intracorneal insert of claim 32, wherein said body comprises a continuous ring.

35. The intracorneal insert of claim 32, wherein said body comprises a sector of a ring covering an arc of at least about 10°.

36. The intracorneal insert of claim 32, wherein said dimension comprises a thickness.

37. The intracorneal insert of claim 32, wherein said dimension comprises a width.

38. An intracorneal insert, said insert substantially following a contour of at least a portion of a ring and having at least one region of added dimension, said region of added dimension generally following said contour and having at least one dimension greater than that of at least one region of said insert adjacent thereto and contiguous therewith.

39. The insert of claim 38, wherein said at least one region comprises at least two regions of added dimension, each of said regions being spaced from one another.

40. The insert of claim 38 further comprising at least one transition zone adjacent to said at least one region of added dimension, said at least one transition zone decreasing in dimension in a direction away from said at least one region of added dimension.

* * * * *